(12) United States Patent
Gaiselmann et al.

(10) Patent No.: US 9,687,270 B2
(45) Date of Patent: Jun. 27, 2017

(54) INSTRUMENT SYSTEM FOR MINIMALLY INVASIVE SURGERY IN SINGLE PORT TECHNOLOGY

(71) Applicants: Thomas Gaiselmann, Villingendorf (DE); Siegfried Riek, Rottweil (DE); Karl-Heinz Bachmann, Villingendorf (DE)

(72) Inventors: Thomas Gaiselmann, Villingendorf (DE); Siegfried Riek, Rottweil (DE); Karl-Heinz Bachmann, Villingendorf (DE)

( * ) Notice: Subject to any disclaimer, the term of this patent is extended or adjusted under 35 U.S.C. 154(b) by 471 days.

(21) Appl. No.: 14/385,084

(22) PCT Filed: Mar. 11, 2013

(86) PCT No.: PCT/EP2013/054914
§ 371 (c)(1),
(2) Date: Sep. 12, 2014

(87) PCT Pub. No.: WO2013/135646
PCT Pub. Date: Sep. 19, 2013

(65) Prior Publication Data
US 2015/0038792 A1  Feb. 5, 2015

(30) Foreign Application Priority Data

Mar. 13, 2012  (DE) .................. 10 2012 203 908

(51) Int. Cl.
*A61B 17/34* (2006.01)
*A61B 17/29* (2006.01)

(52) U.S. Cl.
CPC ...... *A61B 17/3423* (2013.01); *A61B 17/3417* (2013.01); *A61B 17/3421* (2013.01);
(Continued)

(58) Field of Classification Search
CPC ................... A61B 17/3417; A61B 17/3423
See application file for complete search history.

(56) References Cited

U.S. PATENT DOCUMENTS 4,686,965 A * 8/1987 Bonnet .............. A61B 17/0218
                                                    600/104
4,877,033 A   10/1989 Seitz
(Continued)

FOREIGN PATENT DOCUMENTS

DE   3615694   11/1987
DE   8904011    4/1990
(Continued)

OTHER PUBLICATIONS

Patent Cooperation Treaty, "International Search Report" European Searching Authority, document of 3 pages, May 29, 2013.

*Primary Examiner* — Andrew Yang
(74) *Attorney, Agent, or Firm* — Akerman LLP; Peter A. Chiabotti (57) ABSTRACT

An instrument system for minimally invasive surgery in single port technology, having a trocar and at least one instrument channel which runs at the trocar from proximal to distal and a proximal end remaining extra-corporally when the trocar is inserted into the body of a patient, and a distal end located intra-corporally, wherein a semi-flexible instrument can be inserted through the instrument channel in such a manner that the operating handle thereof remains extra-corporal and the distal working element thereof emerges distally from the instrument channel. The instrument channel is flexibly pliant, stable in the longitudinal direction thereof and arranged outside on the trocar. The distal end of the instrument channel is fixed to the trocar.

16 Claims, 4 Drawing Sheets

(52) U.S. Cl.
CPC ............... *A61B 2017/2905* (2013.01); *A61B 2017/3447* (2013.01)

(56) References Cited

U.S. PATENT DOCUMENTS

| | | | |
|---|---|---|---|
| 5,020,514 | A | 6/1991 | Heckele |
| 5,156,142 | A | 10/1992 | Anapliotis et al. |
| 5,259,366 | A | 11/1993 | Reydel et al. |
| 5,562,688 | A * | 10/1996 | Riza ................ A61B 17/0469 606/139 |
| 5,632,717 | A | 5/1997 | Yoon |
| 5,685,820 | A | 11/1997 | Riek et al. |
| 5,916,233 | A | 6/1999 | Chin |
| 6,007,483 | A | 12/1999 | Kieturakis |
| 6,030,365 | A | 2/2000 | Laufer |
| 6,183,485 | B1 | 2/2001 | Thomason et al. |
| 6,352,503 | B1 * | 3/2002 | Matsui ............... A61B 1/00071 600/104 |
| 7,331,971 | B2 | 2/2008 | Kasahara et al. |
| 7,566,300 | B2 | 7/2009 | Devierre et al. |
| 7,604,648 | B2 | 10/2009 | Kerr |
| 2004/0138529 | A1 * | 7/2004 | Wiltshire ............ A61B 1/0055 600/144 |
| 2005/0085691 | A1 | 4/2005 | Nakao |
| 2005/0159764 | A1 | 7/2005 | Kasahara et al. |
| 2005/0267335 | A1 * | 12/2005 | Okada ................. A61B 1/0014 600/173 |
| 2006/0178560 | A1 | 8/2006 | Saadat et al. |
| 2006/0247500 | A1 * | 11/2006 | Voegele ................. A61B 1/32 600/208 |
| 2007/0049963 | A1 | 3/2007 | Kerr |
| 2007/0088247 | A1 | 4/2007 | Bliweis et al. |
| 2007/0270752 | A1 | 11/2007 | Labombard |
| 2007/0293727 | A1 | 12/2007 | Goldfarb et al. |
| 2008/0147002 | A1 | 6/2008 | Gertner |
| 2008/0188868 | A1 | 8/2008 | Weitzner et al. |
| 2008/0294184 | A1 | 11/2008 | Smith |
| 2009/0163768 | A1 | 6/2009 | Ibrahim et al. |
| 2010/0268035 | A1 | 10/2010 | Oberlaender et al. |
| 2011/0118545 | A1 | 5/2011 | Williams et al. |
| 2016/0228107 | A1 * | 8/2016 | Madsen ............ A61B 17/3417 |

FOREIGN PATENT DOCUMENTS

| | | |
|---|---|---|
| DE | 10333956 | 2/2005 |
| DE | 102009018639 | 10/2010 |
| EP | 0369936 | 5/1990 |
| EP | 1977696 | 10/2008 |
| EP | 2133027 | 12/2009 |
| WO | 9965405 | 12/1999 |
| WO | 0101847 | 1/2001 |
| WO | 2004112596 | 12/2004 |
| WO | 2006050047 | 5/2006 |

* cited by examiner

INSTRUMENT SYSTEM FOR MINIMALLY INVASIVE SURGERY IN SINGLE PORT TECHNOLOGY

CROSS REFERENCE TO RELATED APPLICATIONS

This application is a §371 National Phase of PCT/EP2013/054914, filed Mar. 22, 2013, which claims priority to German Patent Application No. 10 2012 203 908.2, filed Mar. 13, 2012, the entireties of which are incorporated by reference herein.

BACKGROUND

The application relates to an instrument system for minimally invasive surgery in single port technology.

SUMMARY

In minimally invasive surgery, access to a body cavity through an incision, such as in the abdominal cavity during laparoscopic surgery, for example. It is through such accesses that the instruments required for the operation and the optic used to illuminate the intracorporeal surgical area and generally transmits an image of the surgical area via a camera to a monitor is inserted. While it has been the practice up to now to create a separate access for each instrument and for the optic, the use of single port technology is on the rise in which only one single access (single port) is created through which the instruments and the optic can be inserted.

For single port technology, it is known (e.g., DE 10 2009 018 639 AI) to implant an adapter into the abdominal wall through which the instruments and the optic are inserted. A relatively large skin incision is required for the implantation of the adapter, which runs counter to the objective of minimally invasive surgery. The implantation requires an elaborate surgical step because the adapter must be inserted in an airtight manner through the abdominal wall and fixed. What is more, the instruments and the optic are substantially axially parallel to each other with little space between then, thus restricting the execution of the surgical steps using the instruments.

An instrument system of the general type mentioned at the outset is known from US 2011/0118545 AI in which instrument channels and an optic are inserted through a common single port sleeve. Flexible instruments are inserted through the instrument channels, with their operating handle remaining extracorporeal and the distal working element of the instruments emerging distally from the instrument channel. The instrument channels can be controlled via a control wire system in order to position the working elements of the instruments. The controlling of the instrument channels is structurally elaborate, which renders cleaning and sterilization difficult on the one hand and makes single use impractical due to the cost on the other hand.

The present disclosure provides an instrument system for minimally invasive surgery in single port technology that requires only one small incision, can be manufactured cost-effectively and enables the handling of instruments with many degrees of freedom.

This present application provides an instrument system with the features and structures recited herein.

Advantageous embodiments are indicated in the subclaims.

The instrument system has a trocar that is used to create the access. The trocar can have any basic structure known from the prior art. The term "trocar" is used here in the general sense. It can be a trocar consisting of a trocar pin and trocar sleeve. The trocar can also be just a trocar pin which, in this case, is particularly an optical trocar. The optical trocar has a transparent distal tip and an inner channel into which an optic is inserted or introduced.

Preferably, the trocar has a trocar sleeve that is inserted by means of the coaxial trocar pin through a skin incision, for example into the abdominal wall. The trocar pin can be embodied as an optical trocar. If a trocar sleeve that forms the access channel is used, an optic is preferably inserted into it that is used to illuminate the surgical area and is equipped to performing imaging and observation with a simple camera or 3D camera. At least one flexibly pliant instrument channel is arranged on the trocar that runs on the outside of the trocar at least in the region remaining intracorporeal when the trocar is inserted. The instrument channel can preferably be a tubular jacket, for example a plastic tube. The instrument channel runs in the longitudinal direction of the trocar. The distal end of the instrument channel is fixed to the distal end of the trocar. The instrument channel is guided in a proximal lengthwise portion in an axially moveable manner on the trocar. The instrument channel has a lateral outlet opening proximally offset against the distal end. A semi-flexible miniature instrument is inserted into the instrument channel at the proximal end and emerges with its distal working element through the outlet opening of the instrument channel. If the instrument channel is pushed in the guide on the trocar in the proximal direction, it rests against the outer wall of the trocar in the region between its distal fixation and the guide. If the instrument channel is pushed in the distal direction in the distal direction, the guide channel bends outwardly in an arched manner as a result of its distal fixation between this fixation and the guide. The outlet opening of the instrument channel is located in the region of this bending. As a result, the semi-flexible instrument emerges from the outlet opening tangentially to the bending of the instrument channel. The farther the instrument channel is pushed in the distal direction, the more pronounced the curvature of the bending of the instrument channel in the distal region becomes. As a result, the outlet opening is increasingly shifted into a region of the instrument channel that is bent distally beyond the distal end of the trocar and is positioned at an increasing angle against the geometric center axis of the trocar. The pitch of the distal end of the instrument emerging tangentially from the instrument channel with respect to the axis of the trocar can thus be varied between 0° and greater than 90°. Here, 0° means parallel to the axis, 90° means perpendicular to the axis, and greater than 90° means that the distal end of the instrument is oriented against the end of the trocar in the proximal direction.

In a preferred embodiment, two instrument channels are provided on the trocar that are arranged diametrically with respect to each other. The instruments guided through these instrument channels are thus arranged with their working elements aligned opposite each other. The pitch of the instruments with respect to the axis of the trocar and with respect to the respective other instrument can be varied independently by moving the respective instrument channel axially. Moreover, by extending the distal end of the respective instrument varying distances out of the associated instrument channel, the radial gap of the respective working element in relation to the trocar axis and in relation to the respective other instrument can be adjusted. By twisting the extracorporeal operating handle, the instruments can be rotated on their axis, so that their distal working elements can also be moved rotatably about the instrument axis. Finally, the trocar itself can be tilted and rotated on its axis, so that the alignment of the instrument channels in relation to the operation site can be freely selected. These different possibilities for adjustment result in additional degrees of freedom for the manipulation of the instrument compared to the prior art.

The instrument system is also suited to a robot-controlled operation. For this purpose, the trocar, the proximal end of the instrument channels and the actuation of the instruments are connected to controllable axes of a robot. The large number of degrees of freedom enables variable and precise manipulation of the working elements of the instruments with a relatively simple control.

If the trocar has only one trocar pin that is embodied as an optical trocar, the working channels are arranged on this trocar pin. By virtue of the optical trocar, the operative intervention can be observed by means of the instrument and kept in view. An embodiment in which the trocar consists of a trocar pin and a trocar sleeve is preferred. In that case, the instrument channels are arranged on the trocar sleeve. The trocar sleeve with the instrument channels is inserted by means of the trocar pin. The trocar pin is then removed and an optic is inserted into the trocar sleeve that enables the surgical area to be illuminated and observed, so that the intervention can be carried out by means of the instrument under supervision.

BRIEF DESCRIPTION OF THE DRAWINGS

The features and structures of the present disclosure are explained in further detail in the following on the basis of an exemplary embodiment shown in the drawings.

FIG. 1 shows the instrument system according to the invention during a laparoscopic intervention.

DETAILED DESCRIPTION OF THE ILLUSTRATED EMBODIMENTS

In the depicted exemplary embodiment, a trocar consists of a trocar sleeve 10 and a massive or optical trocar pin (not shown in the drawing). The trocar is inserted into the patient's abdominal wall 12, with the distal tip of the trocar pin penetrating through an incision in the skin 14 and through the fatty tissue 16, the fascia 17 and the peritoneum 18. As soon as the distal tip of the trocar has passed through the peritoneum 18 into the abdominal cavity, the abdomen is insufflated in most cases. The trocar pin is then pulled out of the trocar sleeve 10, which remains behind as an access into the intracorporeal surgical area in the abdominal wall 12. A valve 20 seals the trocar sleeve 10 to that the insufflation gas does not escape. In this regard, the instrument system is consistent with the prior art.

In single port surgical technique, only one such access is produced, and both the optic that is used to illuminate and observe the surgical area and the instruments used for the surgical intervention are introduced through this single access.

An optic 22 is introduced through the inner lumen of the tubular trocar sleeve 10 that ends distally at the distal end of the trocar sleeve 10. The optic 22 has, for example, an optical fiber 24 that conducts light from an extracorporeal light source to the distal end of the optic in order to illuminate the surgical area. Furthermore, the optic has an imaging system through which the surgical area can be observed. The imaging system can comprise a camera 26, for example, that transmits the image of the surgical areas to a monitor. The imaging can be two-dimensional or even three-dimensional. Such optics 22 are also inherently known prior art.

At least one instrument channel 28 is arranged on the trocar. In the depicted exemplary embodiment, two instrument channels 28 are provided which are arranged in the depicted exemplary embodiment on the trocar sleeve 10 diametrically to each other. The instrument channels 28 are flexibly pliant and stable in their longitudinal direction. As a result of this characteristic, the instrument channels 28 cam absorb compressive and tensile forces in their longitudinal direction. Under the effect of an axial compressive force, the instrument channels 28 bend and arch laterally outward. Preferably, the instrument channels 28 are embodied as tubular jackets such as those that are used as jackets in Bowden cables. The jacket can preferably me made of plastic. Expediently, the instrument channel 28 and optionally the trocar sleeve 10 as well can be made of a transparent material, so that an instrument 38 guided in the instrument channel 28 is visible from the outside and its movement can be followed. The jacket can also be embodied with preferably axially running reinforcements or stiffeners that stabilize the bending of the instrument channel 28 in a shaping manner, so that bending preferably occurs on the plane of curvature, whereas movement out of this plane of curvature is rendered more difficult.

Figure 1:
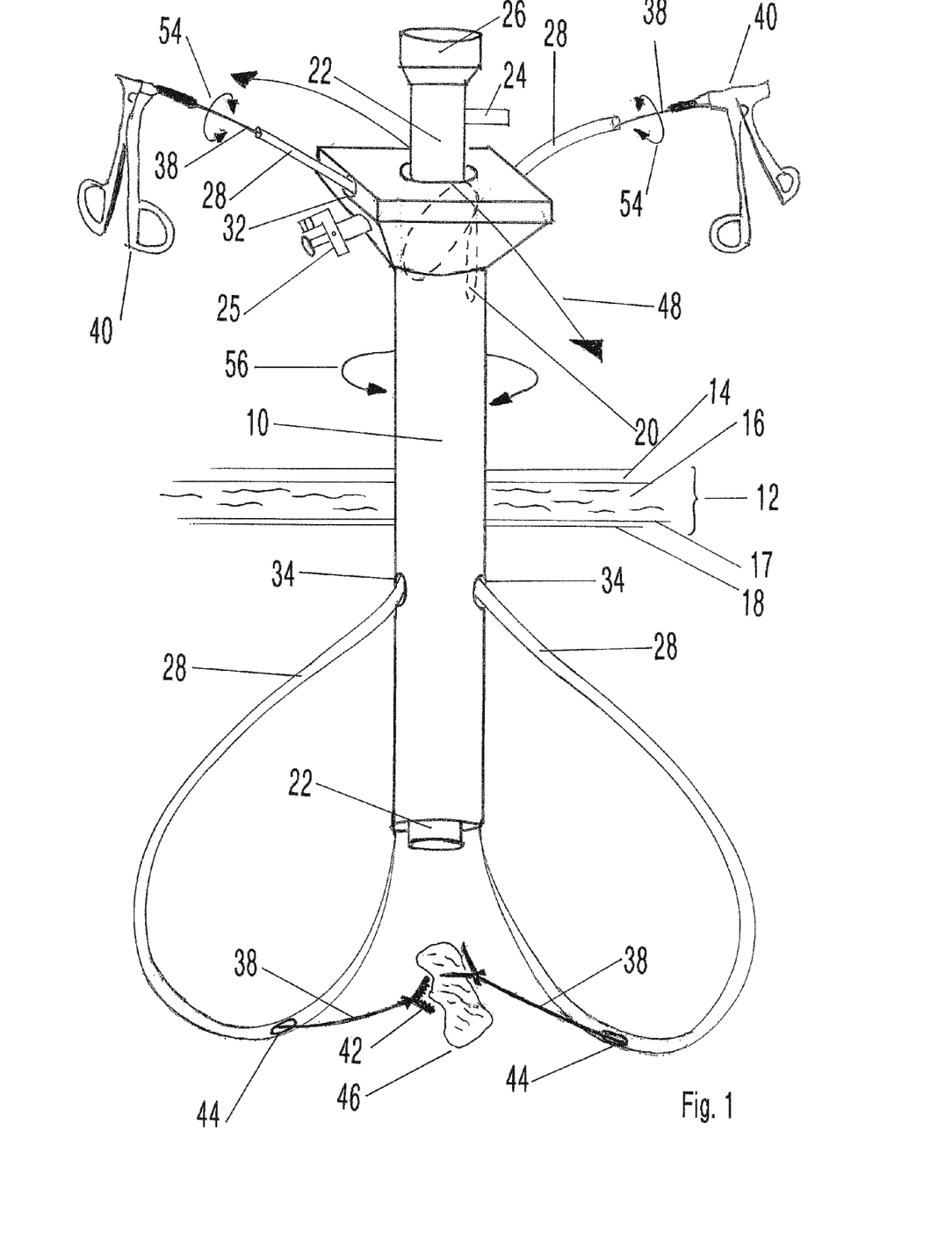
FIG. 1 shows the instrument system according to the present disclosure during a laparoscopic intervention.

The instrument channels 28 are fixed with their distal end 30 to the distal end of the trocar sleeve 10. For this purpose, for example, the distal end 30 of the instrument channel 28 can be bent in the shape of a hairpin and cast or adhered axially with the distal end of the trocar sleeve 10. It is also possible to embody the attachment point of the distal end 30 of the instrument channel 28 such that it can me moved axially on the distal end of the trocar sleeve 10 by means of suitable adjusting means. The instrument channel 28 runs from its fixed distal end 30 freely in the proximal direction along the outside of the trocar sleeve 10. The instrument channel 28 is guided proximally on the trocar in an axially displaceable manner with a middle lengthwise portion. The guide can be embodied in various ways, it being essential that the instrument channel 28 be axially displaceable in relation to the trocar or the trocar sleeve 10 but be held on the trocar or the trocar sleeve 10 in the radial direction. In the depicted embodiment, the guide on the trocar is embodied such that instrument channel 28 enters proximally through an inlet opening 32 into the trocar sleeve 10 and runs on the interior of the trocar sleeve 10 to a distally offset outlet opening 34 through which the instrument channel 28 emerges again on the outside of the trocar sleeve 10. As a result, the instrument channel 28 set in a defined manner by its fixed distal end 30 on the one hand and by the outlet opening 34 on the other hand. In the lengthwise region 36 between the fixed distal end 30 and the guide point defined by the outlet opening 34, the instrument channel 28 can be bent flexibly away from the outer wall of the trocar sleeve 10 and forward beyond the distal end of the trocar sleeve 10. The guide of the instrument channel 28 on the trocar or, in the depicted exemplary embodiment, on the trocar sleeve 10, is embodied such that the inlet opening 32 is located extracorporeally and the outlet opening 34 is located intracorporeally when the trocar is inserted into the abdominal wall 12 as shown in FIG. 1. For insufflation of the abdominal cavity via an insufflation port 25, the instrument channel 28 is preferably guided in a sealed manner in the inlet opening 32, for example through a lip seal.

An instrument 38 can be respectively inserted into the proximal end of the instrument channels 28 for the minimally invasive operation. Such instruments 38 are inherently known in minimally invasive surgery and are often referred to as miniature instruments. The instruments 38 are characterized in that they have a long, semi-flexible shaft in which an operating wire is guided. Here, a "semi-flexible" is to be understood as a shaft that is pliant but has sufficient longitudinal stiffness. An operating handle 40 is arranged at the proximal end of the instrument, for example a scissor handle. A working element is respectively arranged at the distal end of the instrument 38 that can be operated by means of the operating handle 40. Such instruments 38 are known in a wide variety of designs for the respective intended uses. The instruments 38 can be embodied, for example, as scissors, as a clamp, as alligator forceps, as a coagulator, as a needle holder, as a clip applicator, etc. These instruments 38 have a small-diameter semi-flexible shaft and a small-diameter working element 42 of a few millimeters, for example of about 2 mm. The instruments 38 are guided in a sealed manner preferably in the proximal end of the instrument channel 28 for insufflation.

The instrument 38 is inserted into the proximal end of the instrument channel 28 protruding proximally out of the inlet opening 32 and advanced by the instrument channel 28. The instrument channel 28 has in its sheathing at least one lateral outlet opening 44 that is located in the bending-out lengthwise region 36 offset in the proximal direction from the fixed distal end 30 of the instrument channel 28. Distally from the outlet opening 44, the inner lumen of the instrument channel 28 is sealed, so that the instrument channel 28 merges into the outlet opening 44 for the insertion of the instrument 38 into the outlet opening 44. If the instrument 38 is advanced in the instrument channel 28, the distal end of the instrument 38 is pushed out distally with the working element 42 through the outlet opening 44. Due to the semi-flexibility of the shaft of the instrument 38, the distal end of the shaft protrudes tangentially to the arch of the laterally and outwardly arched lengthwise region 36. With the aid of the operating handle 40, which remains extracorporeal, the instrument 38 can be pushed in a targeted manner by the operator in the instrument channel 28 in the longitudinal direction, so that the distal end emerges distally with the working element 42 from the outlet opening 44 to different extents. Moreover, the instrument 38 can be rotated by means of the operating handle 40 in the instrument channel 28 about its longitudinal axis, so that the working element 42 can be rotated about the axis of the instrument shaft. During the operation, the instrument channel 28 can be locked on the proximal inlet opening 32 by appropriate means with respect to axial and rotational movements.

Figure 2:
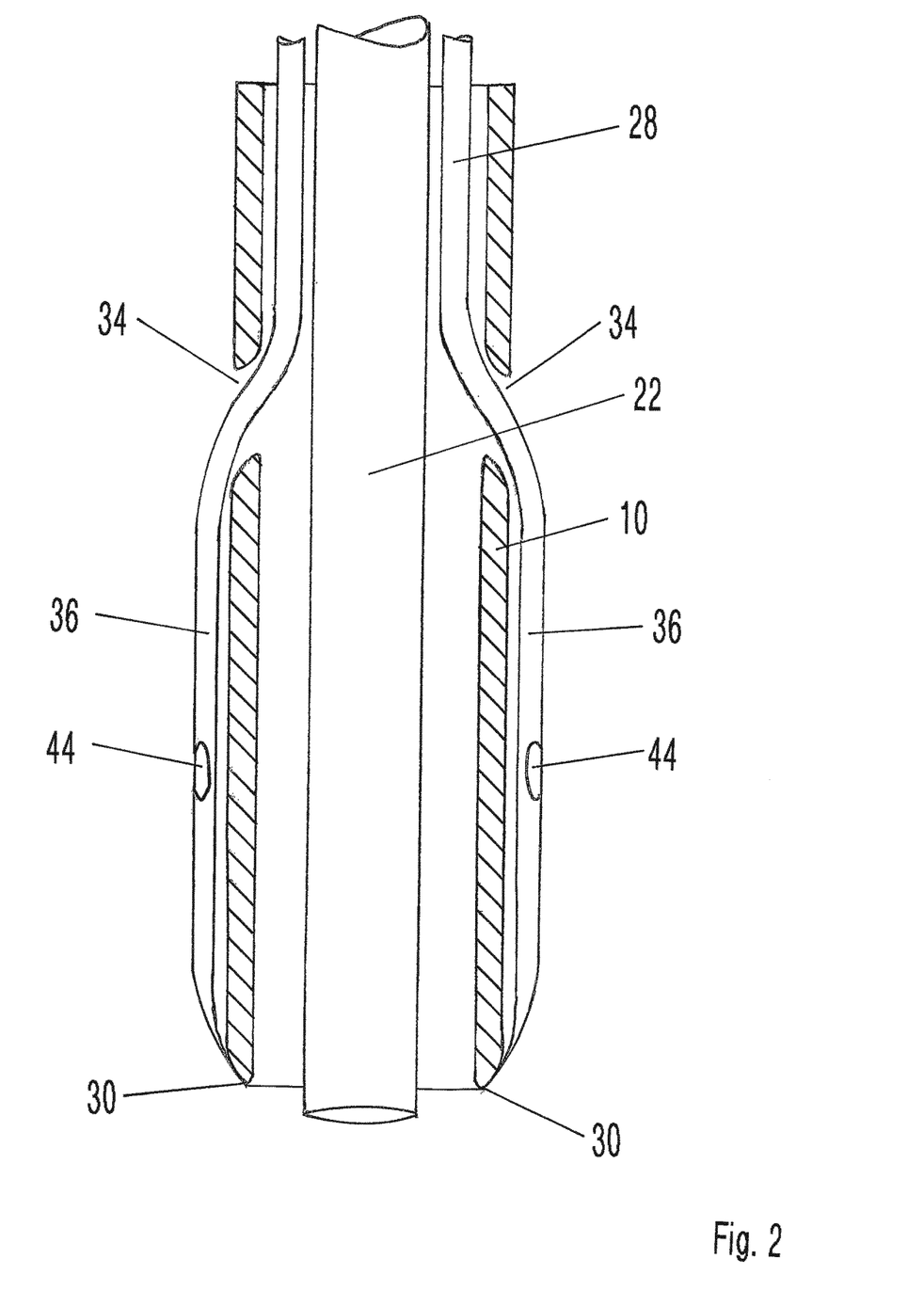
FIGS. 2 to 4 show the distal end of the instrument system with the instrument channels in different positions.

A minimally invasive surgical intervention in single port technology with the instrument system according to the present disclosure is performed in the following steps:

After an incision is made in the skin 14, the trocar is inserted into the abdominal wall 12. For this purpose, the abdominal wall 12 is perforated by means of a trocar pin inserted into the trocar sleeve 10. Upon insertion of the trocar with the trocar sleeve 10, the instrument channels 28 are pulled in the proximal direction, so that the instrument channels 28 rest with their bendable lengthwise region 36 against the outside of the trocar sleeve 10 in a substantially axis-parallel manner, as shown in FIG. 2. The instrument channels 28 thus do not prevent the penetration of the trocar through the abdominal wall 12.

As soon as the trocar is inserted into the abdominal wall 12, the abdominal wall 12 is lifted, for example through insufflation by means of the insufflation port 25, in order to create sufficient free space for the operation. The outlet openings 34 of the guide of the instrument channels 28 is located intracorporeally in the abdomen, whereas the inlet openings 32 are located extracorporeally as shown in FIG. 1. The trocar pin required for the penetration of the abdominal wall 12 and the dilation of the puncture hole is then pulled out of the trocar sleeve 10 and replaced by an optic 22 inserted into the trocar sleeve 10 that is optionally axially adjustable and fixable.

Figure 3:
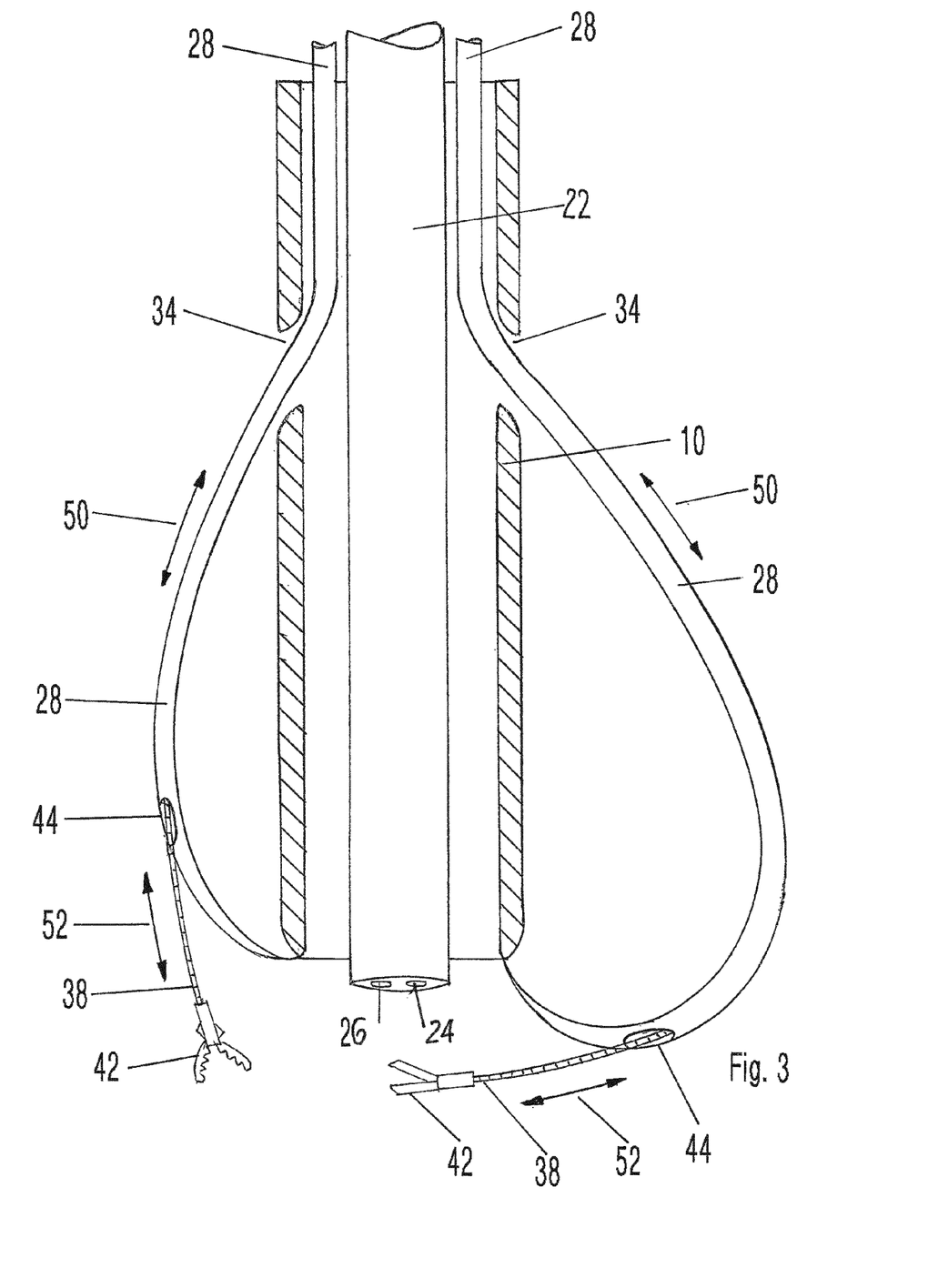
Figure 4:
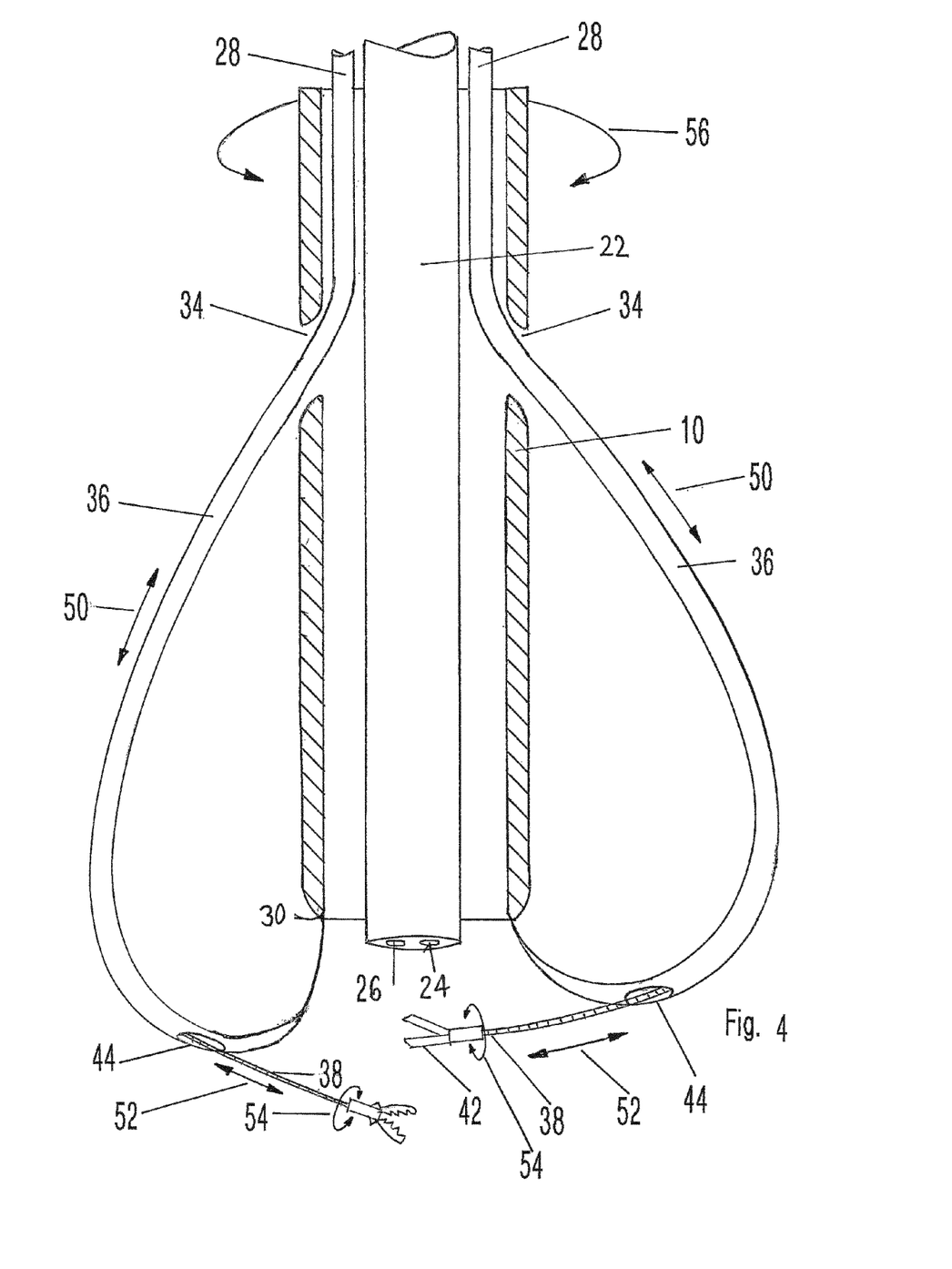

The instrument channels 28 are grasped at their proximally free end and advanced axially in the distal direction by the guide formed by the inlet opening 32 and the outlet opening 34. The lengthwise region 36 of the instrument channels 28 arch increasingly laterally and forward beyond the distal end of the trocar sleeve 10, as is shown in FIG. 3 for the left and right instrument channel 28. The instruments 38 required for the intervention are inserted into the instrument channels 28. The distal end of the instruments 38 with the respective working elements 42 emerges tangentially to the curvature of the bent-out instrument channel 28 through the respective outlet opening 44. As shown in FIG. 3, as the instrument channel 28 is moved farther in the distal direction, the outlet opening 44 travels increasingly into the region of the instrument channel 28, which is bent in a more pronounced manner against the trocar axis. As a result, the pitch between the axis of the distal end of the instrument 38 emerging tangentially from the outlet opening 44 changes increasingly with respect to the center axis of the trocar from about 0° (FIG. 3 left) over about 90° (FIG. 3 right and FIG. 4 left) to about 120°, for example (FIG. 4 right). Here, an angle of 0° means that the distal end of the instrument 38 emerges about parallel to the axis of the trocar, an angle of 90° means that the distal end of the instrument 38 emerges substantially perpendicularly to the center axis of the trocar, while an angle of 120° means that the distal end of the instrument 38 emerges so as to be aligned backward against the distal end of the trocar sleeve 10.

If the instrument channels 28 are bent out so far that the distal ends of the instruments 38 are aligned against the center axis of the trocar sleeve 10 and therefore opposite to each other, the required surgical steps can be performed by means of the working elements 42 on the bodily tissue 46 to be treated, as shown in FIG. 1. The tissue 46 and the working elements 42 are located distally in front of the distal end of the optic 22, so that the surgical area is well illuminated and the intervention can be carried out under optimal vision.

Once the intervention has been completed, the instruments 38 are withdrawn from the instrument channels 28. The instrument channels 28 are pulled back again in the proximal direction so that they lie against the outside of the trocar sleeve 10 as shown in FIG. 2. The trocar sleeve can now be pulled without hindrance out of the puncture opening in the abdominal wall 12.

The instrument system according to the present disclosure enables an extraordinarily large number of degrees of freedom for the use of instruments 38, so that a single-port operation can be performed in an especially versatile and reliable manner. The trocar with the trocar sleeve 10 can be tilted in its angle of insertion in relation to the abdominal wall 12, as shown in FIG. 1 by the arrow 48. As a result, the trocar sleeve 10 can be aligned with the intracorporeal surgical area. The instrument channels 28 can be pushed axially in the guide 32, 34 as indicated by the arrows 50. As a result, the angle of emergence of the distal ends of the instruments 38 can be varied. The instruments 38 can be pushed axially to different extents into the instrument channels 28, as indicated by the arrows 52. As a result, the working elements 42 can be guided in a targeted manner to different distances from the center axis of the instrument system. The instruments 38 can be rotated in the instrument channels 28, so that the working elements 42 can be rotated about the instrument axis as shown by the arrows 54. As a result, the angle of action of the working elements 42 can be varied. Finally, the trocar sleeve 10 can be rotated about its center axis as indicated by the arrow 56. As a result, the instrument channels 28 and hence the direction of action of the working elements 42 can be rotated about the center axis and hence around the intervention site 46.

In the depicted exemplary embodiment, the instrument channels 28 lie against the outside of the sheathing of the trocar sleeve 10 in the retracted position according to FIG. 2. In another embodiment, longitudinal grooves can be provided in the outer sheathing of the trocar sleeve 10 that receive the instrument channels 28 in the retracted position. As a result, the influence of the instrument channels 28 during insertion and withdrawal of the trocar can be additionally reduced.

Moreover, locking means can be provided in the region of the inlet opening 32 that make it possible to block the axial displacement of the instrument channels 28 during the intervention.

In the depicted exemplary embodiment, the trocar has a trocar pin and a trocar sleeve 10 remaining as an access channel into which an optic 22 is inserted. It is also possible to embody the trocar as an optical trocar without a trocar sleeve. In that case, an optic inserted into the trocar pin used for perforation is also used for observing the surgical area during the intervention. In this embodiment, the instrument channels are arranged on the outside of the trocar pin, fixed distally thereto and guided with their middle lengthwise portion against this trocar pin.

LIST OF REFERENCE SYMBOLS

10 trocar sleeve
12 abdominal wall
14 skin
16 fatty tissue
17 fascia
18 peritoneum
20 valve
22 optic
24 optical fiber
25 insufflation port
26 camera
28 instrument channel
30 distal end of 28
32 inlet opening
34 outlet opening
36 lengthwise region
38 instrument
40 operating handle
42 working element
44 outlet opening
46 tissue
48 tilting of the trocar
50 angle of emergence
52 emerging length
54 rotation of the instrument
56 rotation of the trocar

The invention claimed is:

1. An instrument system for minimally invasive surgery in single port technology, comprises:

a trocar with an instrument channel that runs from proximal to distal on the trocar and a proximal end that remains extracorporeal when the trocar is inserted into a body of a patient and a distal end that is located intracorporeally, wherein a semi-flexible instrument can be inserted through the instrument channel in such a way that a operating handle of the semi-flexible instrument remains extracorporeal and a distal working element of the semi-flexible instrument emerges distally from the instrument channel, wherein the instrument channel is flexibly pliant and stable in its longitudinal direction, wherein the distal end of the instrument channel is fixed on the trocar, wherein the instrument channel can be displaced axially and proximally in a guide on the trocar with a middle section, whereby the instrument channel is arranged on an outside of the trocar in its lengthwise region between the fixed distal end and the guide on the trocar and is bent laterally out and away from the trocar and forward beyond the distal end of the trocar when the instrument channel is pushed in the distal direction in the guide, and wherein the instrument channel has an outlet opening for the distal end of the instrument that is located in bending-out lengthwise regions offset in the proximal direction from the fixed distal end.

2. The instrument system of claim 1, wherein the instrument channel comprises a tubular jacket.

3. The instrument system of claim 1, wherein the instrument channel rests in an axis-parallel manner in a non-bent-out state against an outer lateral surface of the trocar.

4. The instrument system of claim 1, wherein the instrument channel runs in the guide within the trocar from an inlet opening that remains extracorporeal to an intracorporeal outlet opening (34).

5. The instrument system of claim 1, wherein two instrument channels are arranged diametrically to each other on the trocar.

6. The instrument system of claim 1, wherein the trocar has a trocar sleeve and a trocar pin that can be inserted therein, wherein the instrument channel is arranged on the trocar sleeve.

7. The instrument system of claim 1, wherein the trocar is equipped with a coaxially insertable optic that can optionally be axially displaced and locked.

8. The instrument system of claim 7, wherein the optic can be inserted into the trocar sleeve after removal of the trocar pin.

9. The instrument system of claim 7, wherein the trocar is an optical trocar with a transparent distal tip in which an optic can be inserted into the trocar pin.

10. The instrument system of claim 1, wherein the instrument channel can be locked on the trocar against axial and rotational movements.

11. The instrument system of claim 1, wherein the instrument is guided in a sealed manner in the instrument channel.

12. The instrument system of claim 4, wherein the instrument channel is guided in a sealed manner in the trocar.

13. The instrument system of claim 1, wherein the distal end of the instrument channel is fixed in an axially displaceable position on the trocar.

14. The instrument system of claim 1, wherein the instrument channel includes a transparent material.

15. The instrument system of claim 7, wherein the optic can be inserted into the trocar sleeve after removal of the trocar pin.

16. The instrument system of claim 1, wherein the instrument channel is received in an outer longitudinal groove of the trocar.

\* \* \* \* \*